(12) United States Patent
Sasaki

(10) Patent No.: US 8,360,960 B2
(45) Date of Patent: Jan. 29, 2013

(54) ENDOSCOPE WITH SURGICAL INSTRUMENT MULTI-POSITIONING CAPABILITY

(76) Inventor: Larry Sasaki, Shreveport, LA (US)

( * ) Notice: Subject to any disclaimer, the term of this patent is extended or adjusted under 35 U.S.C. 154(b) by 413 days.

(21) Appl. No.: 12/798,918

(22) Filed: Apr. 13, 2010

(65) Prior Publication Data
US 2010/0324364 A1 Dec. 23, 2010

Related U.S. Application Data

(60) Provisional application No. 61/212,553, filed on Apr. 13, 2009.

(51) Int. Cl.
*A61B 1/00* (2006.01)
(52) U.S. Cl. .................................................... 600/104
(58) Field of Classification Search ................ 600/104, 600/128, 153, 154
See application file for complete search history.

(56) References Cited

U.S. PATENT DOCUMENTS

| | | | | |
|---|---|---|---|---|
| 6,328,730 | B1* | 12/2001 | Harkrider, Jr. | 604/523 |
| 2006/0282012 | A1* | 12/2006 | McAlister et al. | 600/565 |
| 2007/0088247 | A1* | 4/2007 | Bliweis et al. | 604/22 |
| 2010/0324364 | A1* | 12/2010 | Sasaki | 600/104 |

\* cited by examiner

*Primary Examiner* — W. B. Perkey
(74) *Attorney, Agent, or Firm* — R. Keith Harrison

(57) ABSTRACT

An endoscope having circumferential surgical instrument positioning capability includes an operation portion; an elongated, flexible insertion portion extending from the operation portion; a viewing conduit extending through the operation portion and the insertion portion; a plurality of instrument channels provided in and spaced around a circumference of the insertion portion; and a channel selector sleeve assembly having a selector channel rotatably carried by the operation portion. The selector channel of the channel selector sleeve assembly registers with the plurality of instrument channels, respectively, as the channel selector sleeve assembly is rotated with respect to the insertion portion.

5 Claims, 8 Drawing Sheets

ENDOSCOPE WITH SURGICAL INSTRUMENT MULTI-POSITIONING CAPABILITY

CROSS-REFERENCE TO RELATED APPLICATIONS

This application claims the benefit of and incorporates by reference in its entirety U.S. Provisional Application Ser. No. 61,212,553, Filed Apr. 13, 2009.

FIELD

The present disclosure generally relates to endoscopes. More particularly, the present disclosure relates to an endoscope through which a surgical instrument can be inserted and placed at a selected one of multiple positions around the circumference of the endoscope.

BACKGROUND

Endoscopes are extensively used in the examination and surgical treatment of interior body cavities such as the esophagus, stomach, small intestine and large intestine. Generally, an endoscope may include a control portion having a handle fitted with finger-actuated control features and an elongated, flexible, tubular insertion portion which extends from the control portion. The insertion portion may terminate in a viewing window which enables an operator of the endoscope to view the interior body cavity or cavities of the patient into which the endoscope is inserted. An irrigation nozzle at the end of the insertion portion may maintain clarity of the viewing window by ejecting irrigation fluid against and washing body fluids and the like from the window. A suction nozzle at the end of the insertion portion may facilitate suction and removal of irrigation fluid and body fluid from the viewing window.

Some laparoscopes may be fitted with a instrument-receiving channel through which a surgical instrument can be inserted to perform surgical procedures in the body cavity in which the endoscope is inserted. However, conventional laparoscope designs may not facilitate placement of the surgical instrument at the desired position around the circumference of the endoscope relative to the viewing window according to the preference of the laparoscope operator. Therefore, an endoscope having circumferential surgical instrument positioning capability is needed.

SUMMARY

The present disclosure is generally directed to an endoscope having circumferential surgical instrument positioning capability. An illustrative embodiment of the endoscope includes an operation portion; an elongated, flexible insertion portion extending from the operation portion; a viewing conduit extending through the operation portion and the insertion portion; a plurality of instrument channels provided in and spaced around a circumference of the insertion portion; and a channel selector sleeve assembly having a selector channel rotatably carried by the operation portion. The selector channel of the channel selector sleeve assembly registers with the plurality of instrument channels, respectively, as the channel selector sleeve assembly is rotated with respect to the insertion portion.

BRIEF DESCRIPTION OF THE DRAWINGS

The disclosure will now be made, by way of example, with reference to the accompanying drawings, in which.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the claims. Furthermore, there is no intention to be bound by any expressed or implied theory presented in the preceding technical field, background, brief summary or the following detailed description.

Figure 1:
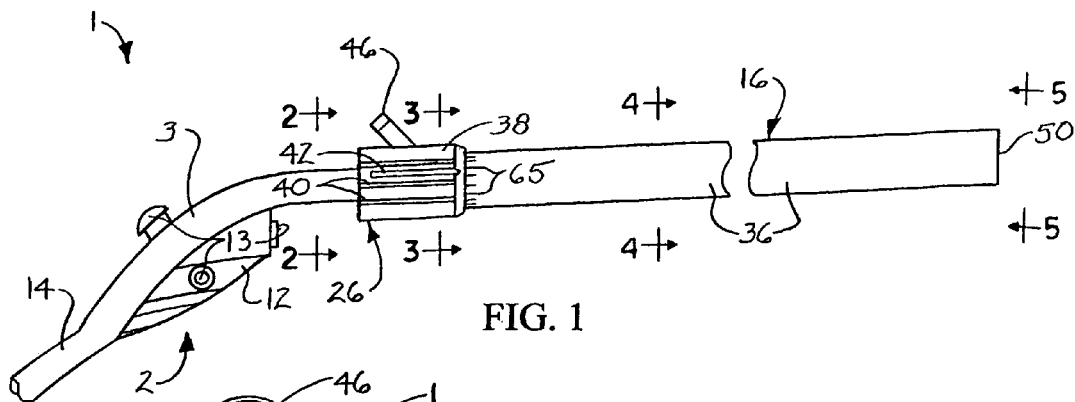
FIG. 1 is a side view of an illustrative embodiment of the endoscope with surgical instrument multi-positioning capability.
Figure 2:
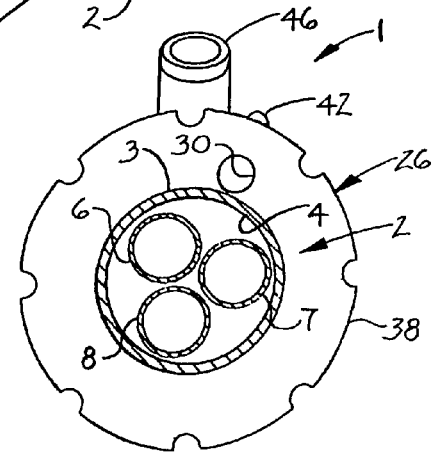
FIG. 2 is a sectional view of an operation portion of an illustrative embodiment of the endoscope, taken along section lines 2-2 in FIG. 1.
Figure 3:
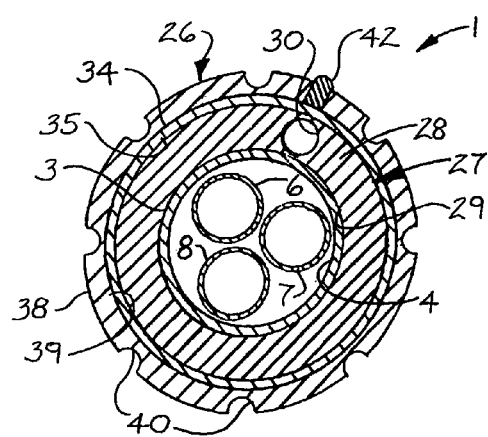
FIG. 3 is a sectional view of a channel selector sleeve assembly portion of an illustrative embodiment of the endoscope, taken along section lines 3-3 in FIG. 1.

Referring initially to FIGS. 1-8 and 14 of the drawings, an illustrative embodiment of the endoscope with surgical instrument multi-positioning capability, hereinafter endoscope, is generally indicated by reference numeral 1. As illustrated in FIG. 1, the endoscope 1 may generally include an operation portion 2 and an elongated, flexible insertion portion 16 which extends from the operation portion 2. The operation portion 2 may include an operation conduit 3 having an operation conduit lumen 4 (FIG. 2). A handle 12 may be provided on the operation conduit 3. The handle 12 may be fitted with finger-actuated endoscope controls 13 as is known by those skilled in the art to facilitate operation and control of the endoscope 1. An endoscope conduit 14 may connect the operation conduit 3 to various components of an endoscope control system 70 (FIG. 16) as will be hereinafter further described. As illustrated in FIGS. 2 and 3, a viewing conduit 6; an irrigation conduit 7; and a suction conduit 8 may extend through the operation conduit lumen 4 of the operation conduit 3 for purposes which will be hereinafter described.

Figure 4:
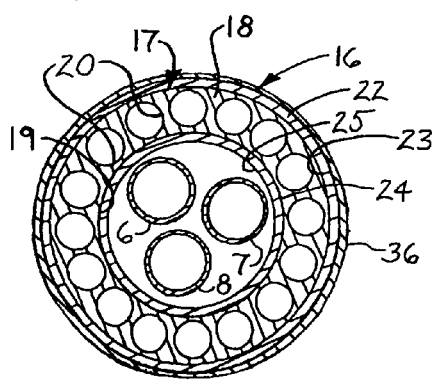
FIG. 4 is a sectional view of an insertion portion of an illustrative embodiment of the endoscope, taken along section lines 4-4 in FIG. 1.
Figure 5:
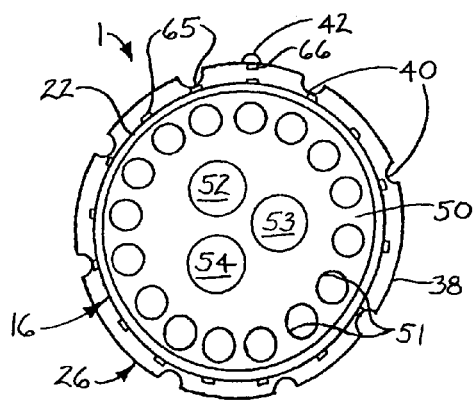
FIG. 5 is an end view of the insertion portion of an illustrative embodiment of the endoscope, taken along viewing lines 5-5 in FIG. 1.

As illustrated in FIG. 4, the insertion portion 16 of the endoscope 1 may include an elongated, flexible insertion conduit 24 having an insertion conduit lumen 25 which communicates with and may be continuous with the operation conduit lumen 4 (FIG. 2) of the operation conduit 3 in the operation portion 2. The viewing conduit 6, the irrigation conduit 7 and the suction conduit 8 may extend through the insertion conduit lumen 25 of the insertion conduit 24. An elongated, flexible channel conduit 17 may have a channel conduit wall 18 which defines a channel conduit lumen 19 through which the insertion conduit 24 extends. Multiple, adjacent instrument channels 20 may extend longitudinally through the channel conduit wall 18 around the circumference of the channel conduit 17 for purposes which will be hereinafter described. While sixteen instrument channels 20 are shown for illustrative purposes in FIG. 4, it is to be understood that the channel conduit 17 may have a lesser or greater number of instrument channels 20. An elongated, flexible light conduit 22 may have a light conduit lumen 23 through which the channel conduit 17 extends. The light conduit 22 may be a fiber optic or other material which is capable of transmitting and emitting light. In some embodiments, the light conduit 22 may be contained in a flexible cover 36. As illustrated in FIG. 5, the light conduit 22 may be exposed at the end of the irrigation portion 16. As is known by those skilled in the art, the insertion portion 16 may be provided with any type of directional control system (not illustrated) which is suitable to facilitate directional control of the insertion portion 16 as it is extended into and through the body cavity of the patient.

As further illustrated in FIG. 5, in some embodiments an end cover 50 may be provided on the end of the irrigation portion 16. Multiple channel openings 51 may extend through the end cover 50 and communicate with the respective instrument channels 20 (FIG. 4) provided in the channel conduit 17 of the insertion portion 16. A transparent viewing window 52 may be provided on the end cover 50 over the viewing conduit 6 (FIG. 4). An irrigation nozzle 53 and a suction nozzle 54 may be provided in the end cover 50 in fluid communication with the irrigation conduit 7 and the suction conduit 8, respectively.

A channel selector sleeve assembly 26 is provided on the operation portion 2 generally at the junction between the operation portion 2 and the insertion portion 16. As illustrated in FIG. 3, the channel selector sleeve assembly 26 may include a selector channel sleeve 27 having a selector channel sleeve wall 28 which defines a selector channel sleeve lumen 29. The operation conduit 3 may extend through the selector channel sleeve lumen 29. A selector channel 30 may extend longitudinally through the selector channel sleeve wall 28 in generally parallel relationship with respect to the longitudinal axis of the selector channel sleeve lumen 29. A light transmission sleeve 34 has a light transmission sleeve lumen 35 through which the selector channel sleeve 27 may extend. The light transmission sleeve 34 may be a fiber optic or other material which is capable of transmitting light. An outer sleeve 38 has an outer sleeve lumen 39 through which the light transmission sleeve 34 may extend. In some embodiments, multiple sleeve grip notches 40 may be provided in the outer sleeve 38. The selector channel sleeve 27, the light transmission sleeve 34 and the outer sleeve 38 are rotatable with respect to the operation conduit 3.

As illustrated in FIGS. 1 and 2, in some embodiments a light source connector 46 may extend from the outer sleeve 38 of the channel selector sleeve assembly 26. The light source connector 46 may be disposed in light-transmitting relationship with respect to the light transmission sleeve 34 (FIG. 3) of the channel selector sleeve assembly 26. A light source 78 (FIG. 16) of the endoscope control system 70 may be adapted for connection to the light source connector 46 for illumination purposes as will be hereinafter described. In some embodiments, a light source connector 46 may be disposed in direct light-transmitting relationship with respect to the light conduit 22 (FIG. 4) and may extend from the cover 36 of the insertion portion 16.

Figure 6:
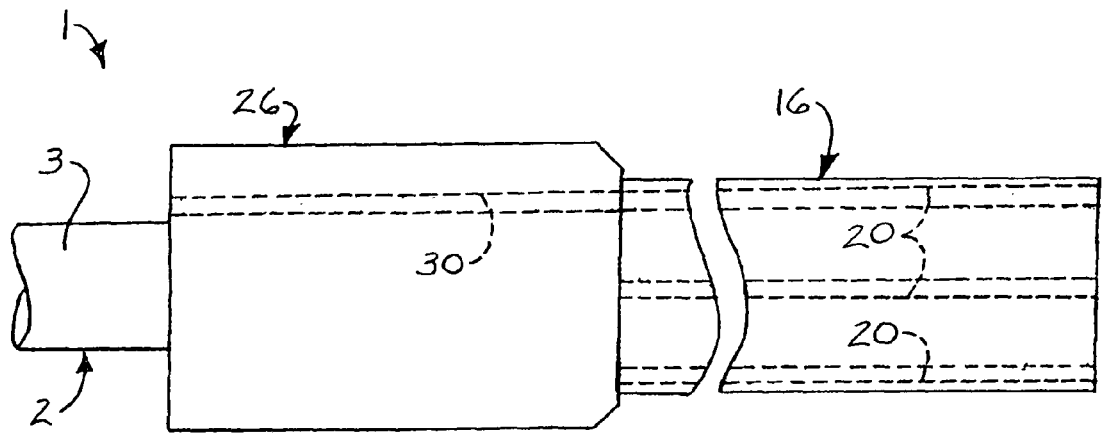
FIGS. 6-8 are respective side views, partially in section, of an illustrative embodiment of the endoscope, more particularly illustrating alignment of a selector channel (shown in phantom) in a channel selector sleeve assembly with different circumferential instrument channels (shown in phantom) provided in an insertion section of the endoscope.
Figure 7:
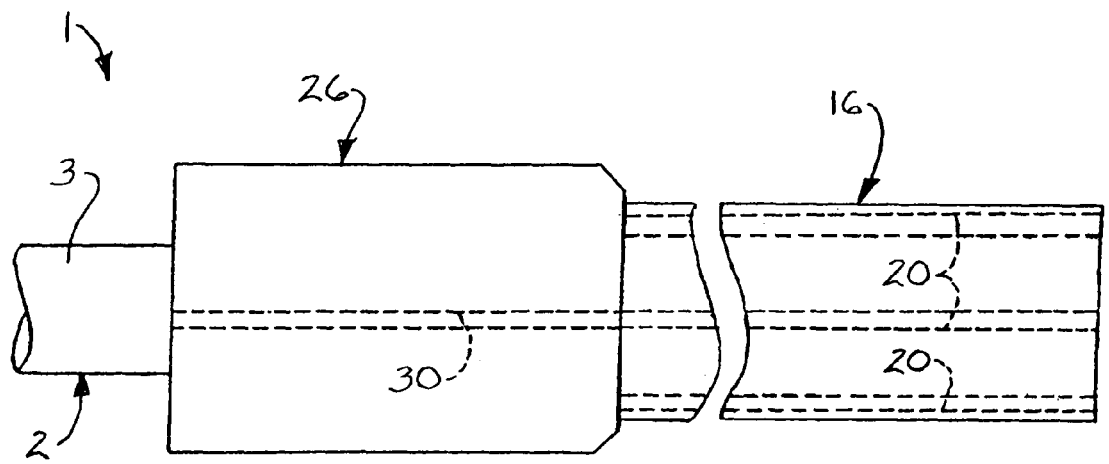
Figure 8:
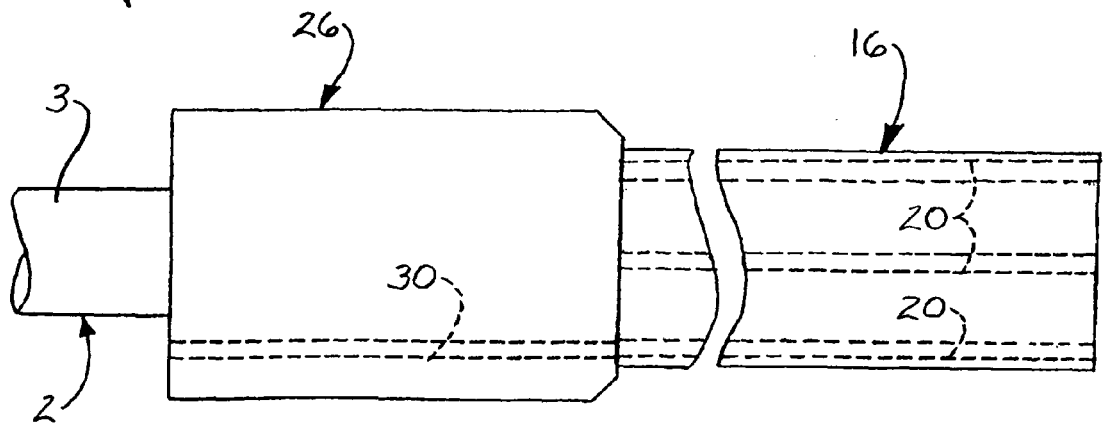

As illustrated in FIGS. 6-8, the selector channel 30 in the channel selector sleeve assembly 26 registers with each of the instrument channels 20 in the insertion portion 16 as the channel selector sleeve assembly 26 is rotated on the operation portion 2. Accordingly, the selector channel 30 may be selectively, individually and successively positioned in registering relationship with respect to the respective instrument channels 20 by rotating the channel selector sleeve assembly 26 on the operation portion 2.

Figure 14:
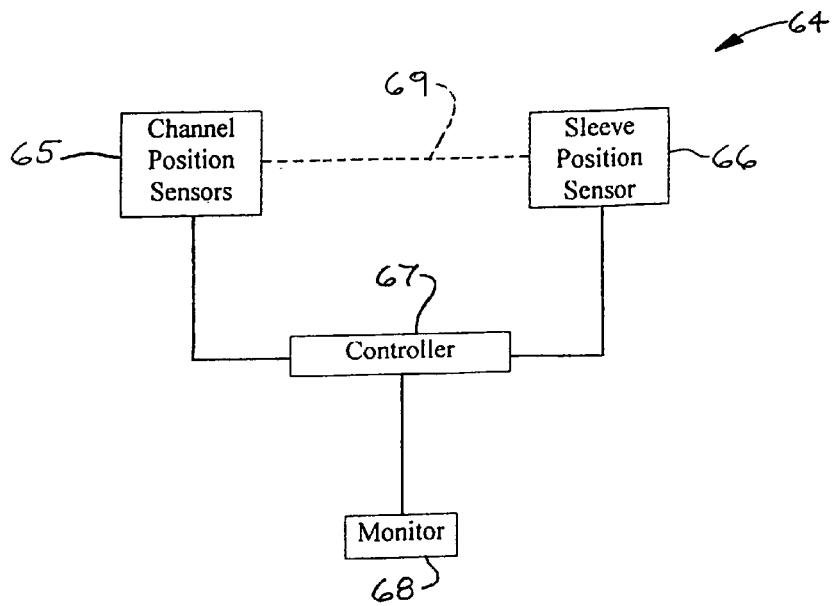
FIG. 14 is a block diagram of an illustrative channel indicator system of an illustrative embodiment of the endoscope.
Figure 15:
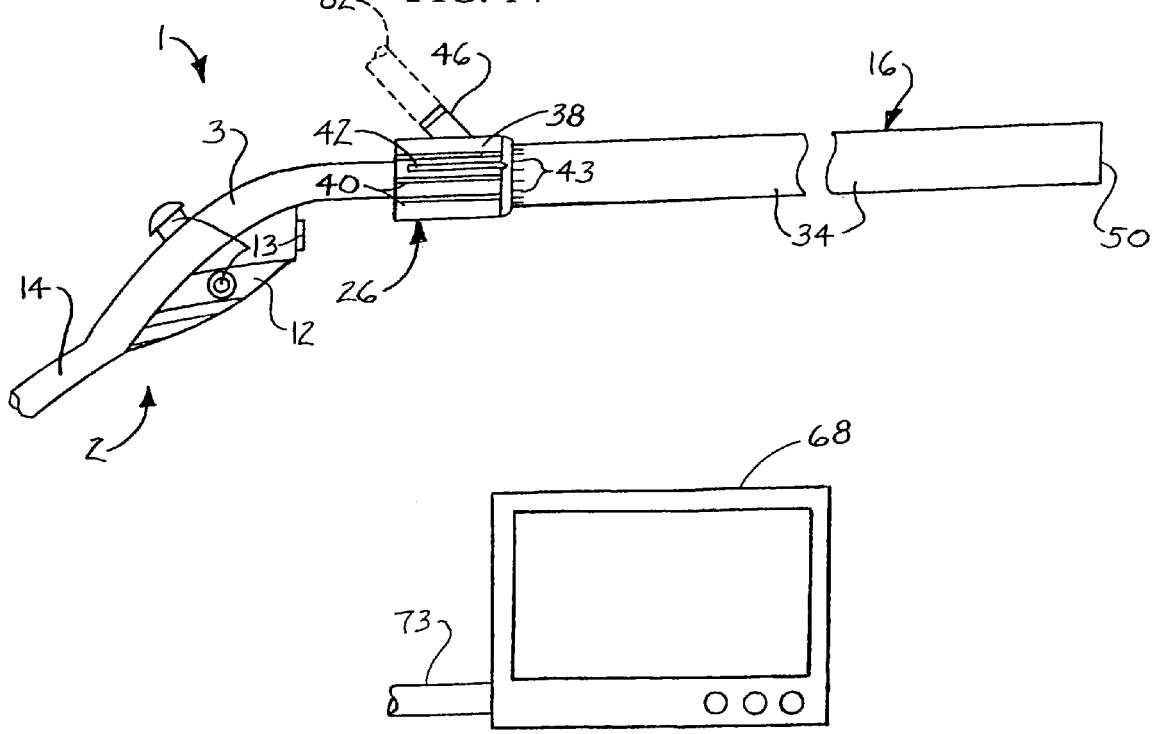
FIG. 15 is a side view of an illustrative embodiment of the endoscope, with a monitor connected to the endoscope.

As illustrated in FIGS. 1, 5 and 14, in some embodiments, the endoscope 1 may include a channel indicator system 64 (FIG. 14) that indicates with which of the instrument channels 20 the selector channel 30 registers on a monitor 68. The channel indicator system 64 may include multiple channel position sensors 65 which are spaced around the exterior circumference of the insertion portion 16, as illustrated in FIG. 5, adjacent to the channel selector sleeve assembly 26, as illustrated in FIG. 1. The channel position sensors 65 correspond in position to the respective instrument channels 20 in the insertion portion 16. A sleeve position sensor 66 is provided on the channel selector sleeve assembly 26 and corresponds in position to the selector channel 30 (FIG. 2). A controller 67 may interface with the channel position sensors 65 and the sleeve position sensor 66. The monitor 68 may interface with the controller 67.

As the channel selector sleeve assembly 26 is rotated on the operation conduit 3 of the operation portion 2, the sleeve position sensor 66 is successively rotated into adjacent proximity to each channel position sensor 65 as the selector channel 30 successively registers with each instrument channel 20. The sleeve position sensor 66 interfaces with each channel position sensor 65 through a magnetic or other connection 69 (FIG. 14). The controller 67 receives data from the channel position sensor 65 and/or the sleeve position sensor 66 which indicates which of the instrument channels 20 registers with the selector channel 30. The controller 67 may use the data to indicate which of the instrument channels 20 registers with the selector channel 30 in a visual format on the monitor 68. The magnetic connection 69 between the sleeve position sensor 66 and each channel position sensor 65 is broken as the sleeve position sensor 66 is rotated out of proximity to each channel position sensor 65 and into proximity to the next channel position sensor 65, with which the sleeve position sensor 66 interfaces through the magnetic connection 69.

In some embodiments, a channel indicator 42 may be provided on the outer sleeve 38 of the channel selector sleeve assembly 26 and may be aligned with the sleeve position sensor 66, as illustrated in FIG. 5. The channel indicator 42 may be a fiber optic or other material which is capable of receiving and emitting light and in some embodiments may be generally elongated, as illustrated in FIG. 1. As illustrated in FIG. 3, the channel indicator 42 may be disposed in light-receiving relationship with respect to the light transmission sleeve 34. Accordingly, as illustrated in FIG. 1, the channel indicator 42 may be aligned with one of the channel position sensors 65 to visually indicate with which of the instrument channels 20 the selector channel 30 registers.

Figure 16:
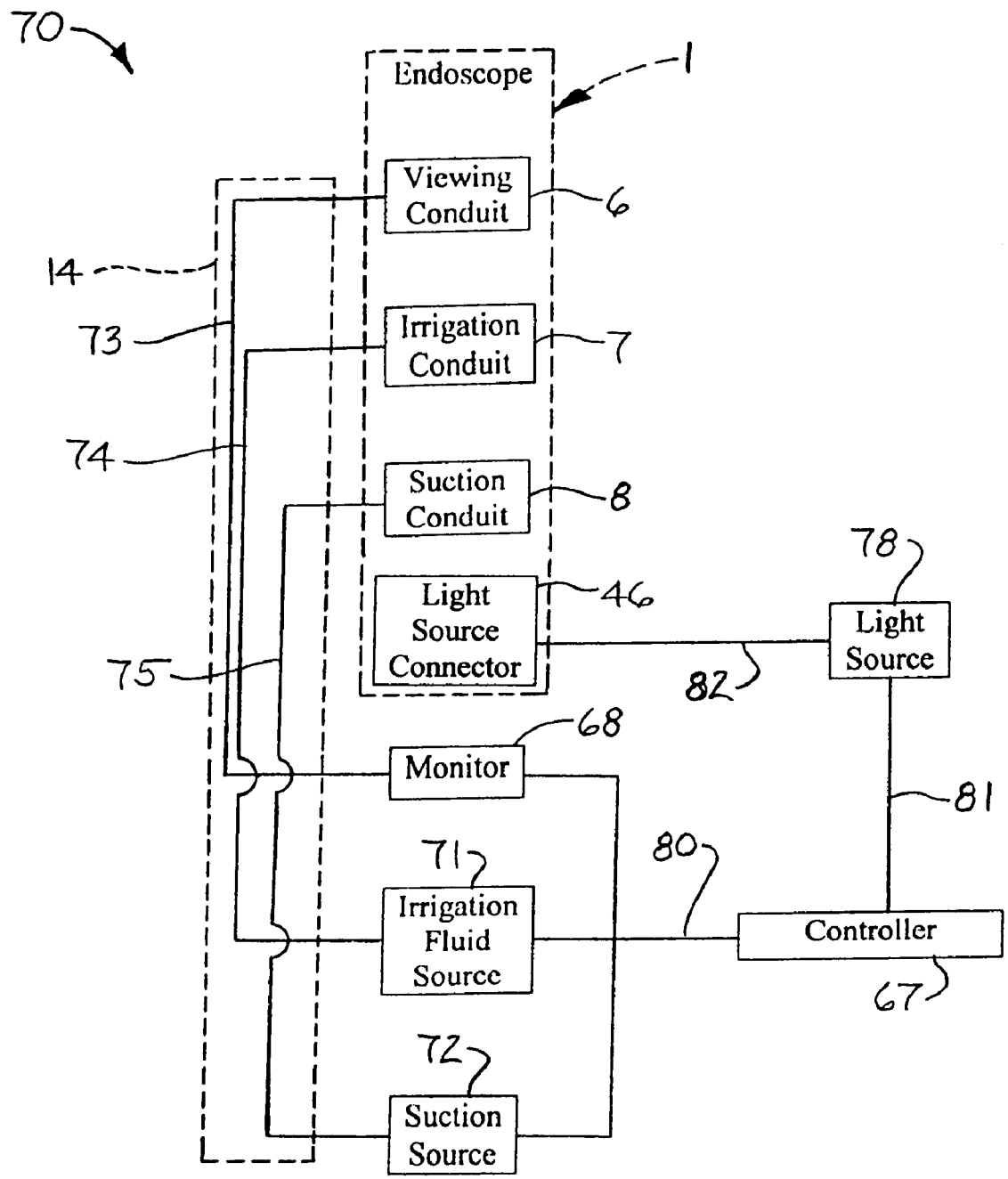
FIG. 16 is a block diagram which illustrates an exemplary control system for an illustrative embodiment of the endoscope.
Figure 17:
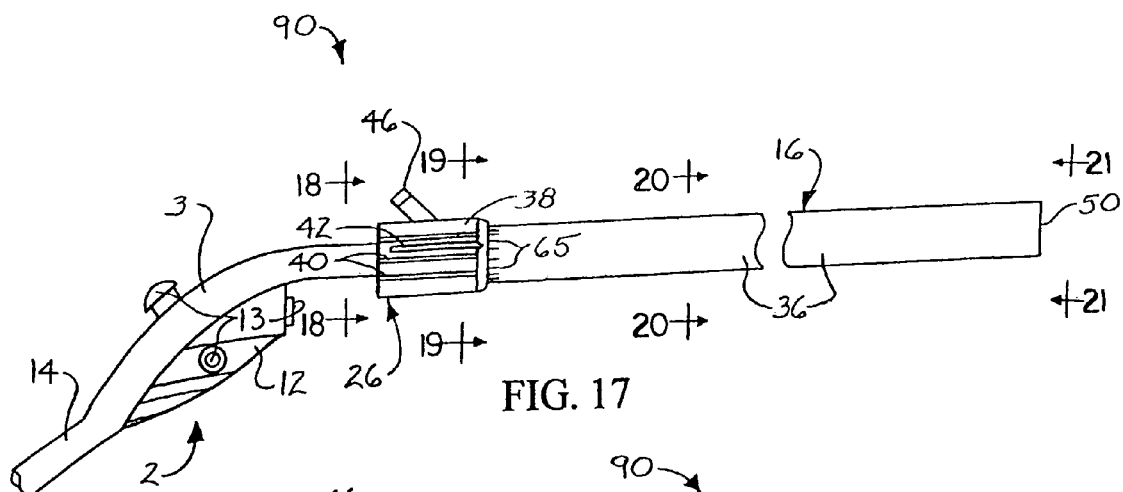
FIG. 17 is a side view of an alternative illustrative embodiment of the endoscope with surgical instrument multi-positioning capability.
Figure 18:
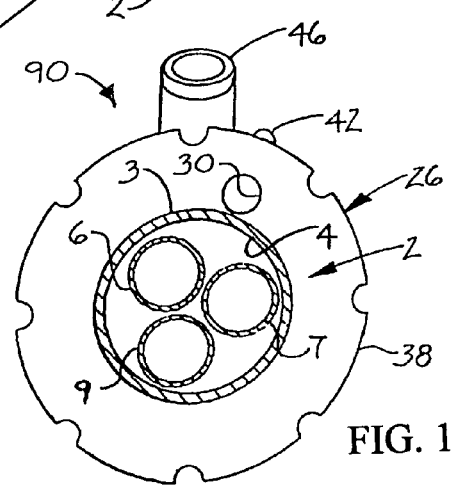
FIG. 18 is a sectional view of an operation portion of the alternative illustrative embodiment of the endoscope, taken along section lines 18-18 in FIG. 17.
Figure 19:
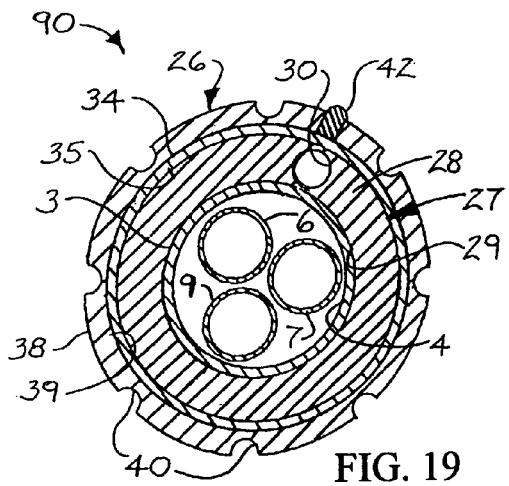
FIG. 19 is a sectional view of a channel selector sleeve assembly portion of the alternative illustrative embodiment of the endoscope, taken along section lines 19-19 in FIG. 17.

Referring next to FIG. 16, the endoscope control system 70 may include a monitor 68 which is connected to the viewing conduit 6 of the endoscope 1 through a viewing cable 73. An irrigation fluid source 71 may be connected to the irrigation conduit 7 through an irrigation fluid delivery conduit 74. A suction source 72 may be connected to the suction conduit 8 through a suction delivery conduit 75. The viewing cable 73, the irrigation fluid delivery conduit 74 and the suction delivery conduit 75 may be contained in the endoscope conduit 14 (shown in phantom).

A light source 78 may be connected to the light source connector 46 of the endoscope 1 such as through a fiber optic light cable 82. A controller 67 may be connected to the monitor 68, the irrigation fluid source 71 and the suction source 72 through a suitable electrical connection 80. The controller 67 may be connected to the light source 78 through an electrical connection 81. In some embodiments, the endoscope controls 13 (FIG. 1) provided on the handle 12 of the endoscope 1 may be connected to the controller 67 for manual operation of one or more of the monitor 68, the irrigation fluid source 71, the suction source 72 and the light source 78. Accordingly, in operation of the endoscope 1, which will be hereinafter further described, a surgical or examination field which is sighted through the viewing window 52 (FIG. 5) of the endoscope 1 may be viewed on the monitor 68. Irrigation fluid (not illustrated) can be pumped from the irrigation fluid source 71, through the irrigation fluid delivery conduit 74 and the irrigation conduit 7, respectively, and discharged from the irrigation nozzle 53 (FIG. 5) of the endoscope 1. The suction source 72 can apply suction to the suction nozzle 54 (FIG. 5) of the endoscope 1 through the suction delivery conduit 75 and the suction conduit 8 of the endoscope 1, respectively.

Referring next to FIGS. 6-16 of the drawings, in typical operation the endoscope 1 may be used to examine and/or perform surgical procedures in a body cavity (not illustrated) such as the esophagus, stomach, small intestine or large intestine of a patient (not illustrated). Accordingly, the light source 78 (FIG. 16) may be connected to the light source connector 46 of the endoscope 1 through the light cable 82, as further illustrated in FIG. 15. The monitor 68, the irrigation fluid source 71 and the suction source 72 may be connected to the viewing conduit 6, the irrigation conduit 7 and the suction conduit 8 through the viewing cable 73, the irrigation fluid delivery conduit 74 and the suction delivery conduit 75, respectively.

An operator (not illustrated) of the endoscope 1 grips the handle 12 as the insertion portion 16 is inserted into the body cavity (not illustrated). Images of the examination and/or surgical field inside the body cavity of the patient may be received through the viewing window 52 (FIG. 5) and displayed on the monitor 68. Irrigation fluid (not illustrated) from the irrigation fluid source 71 may be discharged from the irrigation nozzle 53 (FIG. 5) and against the viewing window 52 to maintain clarity of the viewing window 52 by operation of the irrigation fluid source 71 via the controller 67 (FIG. 16). Suction from the suction source 72 may be applied to remove the discharged irrigation fluid from the viewing window 52 by operation of the suction source 72 via the controller 67. Throughout operation of the endoscope 1, light may be emitted from the light source 78 and through the light cable 82 (FIG. 16), the light source connector 46, the light transmission sleeve 34 (FIG. 3) in the channel selector sleeve assembly 26 and the light conduit 22 (FIG. 4) in the insertion portion 16 of the endoscope 1. The light may be discharged from the light conduit 22 at the end of the insertion portion 16 to illuminate the examination and/or surgical field in the body cavity of the patient.

Figure 9:
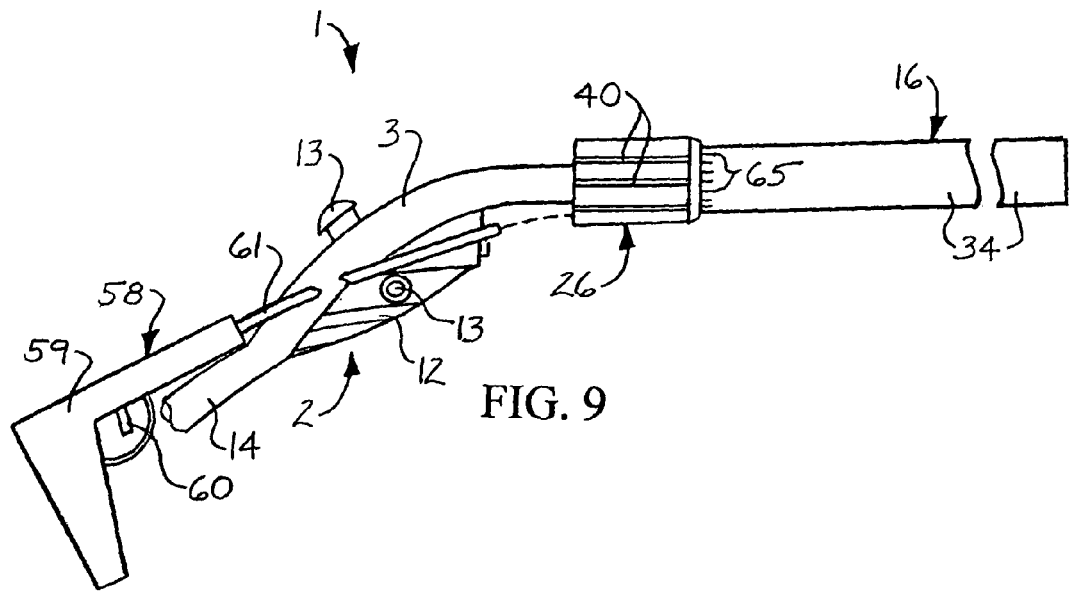
FIG. 9 is a side view, partially in section, of an illustrative embodiment of the endoscope, more particularly illustrating insertion of a surgical instrument (shown in section) into the selector channel (not illustrated) in the channel selector sleeve.
Figure 13:
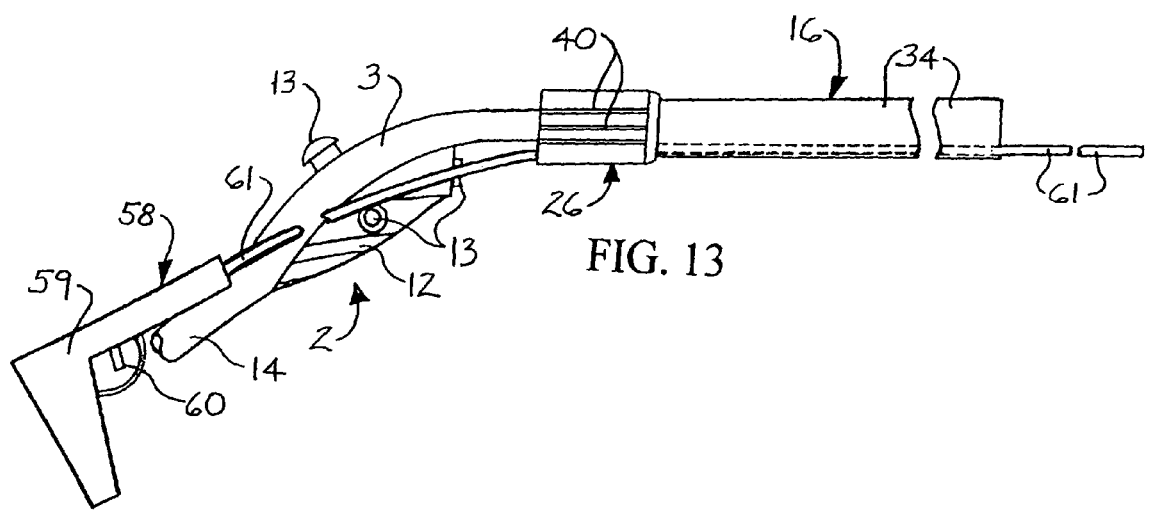
FIG. 13 is a side view, partially in section, of an illustrative embodiment of the endoscope, with the surgical instrument (partially in section) inserted through the selector channel in the channel selector sleeve and through the selected registering instrument channel in the insertion section of the endoscope.

In some medical procedures, it may be deemed necessary to perform various surgical operations using the endoscope 1. Accordingly, as illustrated in FIGS. 9 and 13, a surgical instrument 58, which may be conventional, may be used in conjunction with the endoscope 1 to facilitate implementation of various surgical operations in the body cavity of the patient. Generally, the surgical instrument 58 may include a instrument handle 59 fitted with a finger-actuated trigger 60 and may additionally or alternatively include other control features (not illustrated). A flexible instrument shaft 61 in which is contained the operating element or elements (not illustrated) of the surgical instrument 68 may extend from the instrument handle 59. The operating element or elements of the surgical instrument 58 may be operated by actuation of the trigger 60.

Figure 10:
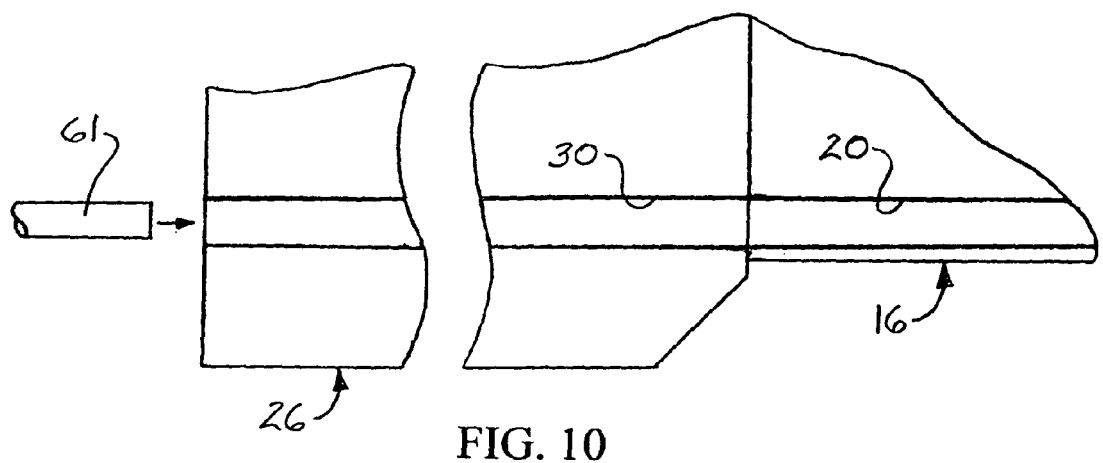
FIGS. 10-12 are respective side views, partially in section, of an illustrative embodiment of the endoscope, more particularly illustrating insertion of the surgical instrument first into the selector channel (FIG. 10) provided in the channel selector sleeve and then into a selected registering instrument channel (FIGS. 11 and 12) provided in the insertion section of the endoscope.
Figure 11:
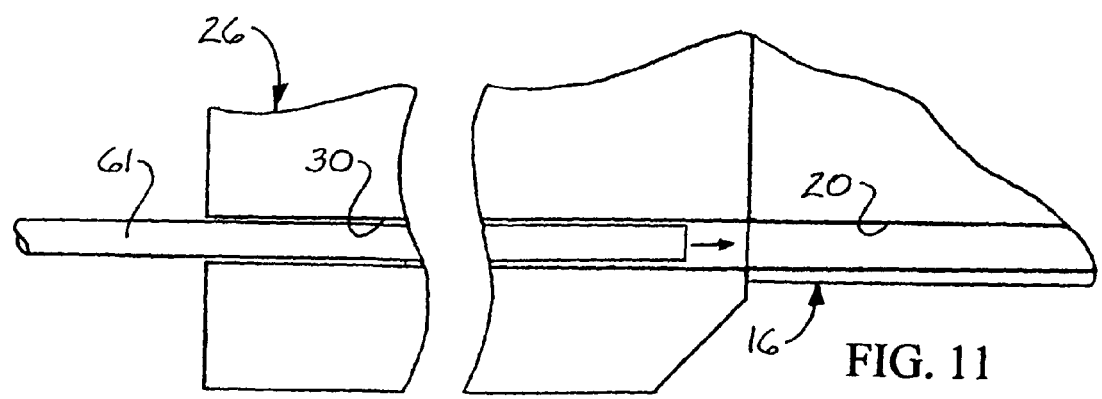
Figure 12:
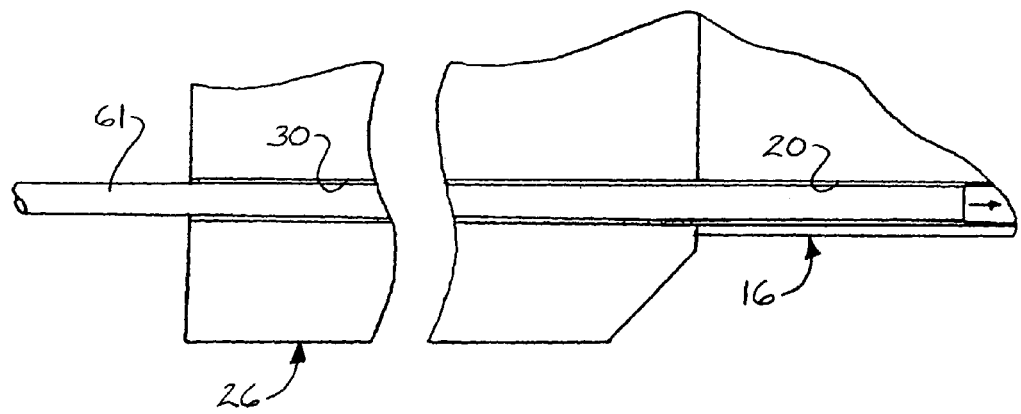

As illustrated in FIGS. 6-8, the channel selector sleeve assembly 26 may be rotated with respect to the insertion portion 16 of the endoscope 1 to register the selector channel 30 in the channel selector sleeve assembly 26 with a selected one of the instrument channels 20 in the insertion portion 16. The instrument channel 20 which is selected for registration with the selector channel 30 corresponds to the desired position of the instrument shaft 61 of the surgical instrument 58 around the circumference of the insertion portion 16 according to the preference of the operator of the endoscope 1 during the surgical procedure. Factors that determine which of the instrument channels 20 is selected for registration with the selector channel 30 may include the particular location of the area in which the surgical operation is to be carried out within the examination or surgical field sighted through the viewing window 52 (FIG. 5) of the endoscope 1. Once the selector channel 30 is rotated into registry with the selected instrument channel 20, the instrument shaft 61 of the surgical instrument 58 may be inserted first through the selector channel 30 in the channel selector sleeve assembly 26, as illustrated in FIGS. 9-11, and then into and through the selected instrument channel 20, as illustrated in FIG. 12. The instrument shaft 61 of the surgical instrument 58 may protrude from the channel opening 51 (FIG. 5) that corresponds to the selected instrument channel 20, as illustrated in FIG. 13. Accordingly, the operator of the endoscope 1 may operate the instrument 58 to perform the surgical operation in the body cavity of the patient typically by manipulation of the trigger 60 and/or other control features (not illustrated) on the surgical instrument 58. In some applications, the instrument shaft 61 of the surgical instrument 58 may be removed from the selected instrument channel 20, and the instrument shaft 61 of the same or a different surgical instrument 58 may be inserted in the same or another selected instrument channel 20 depending on the preferences of the operator of the endoscope 1 and the requirements of the surgical operation.

It will be appreciated by those skilled in the art that the channel indicator 42 on the channel selector sleeve assembly 26 may register with one of the channel position sensors 65 on the insertion portion 16 of the endoscope 1 to indicate the circumferential position of the instrument channel 20 which is selected for insertion of the instrument shaft 61 of the surgical instrument 58. Light from the light transmission sleeve 34 (FIG. 3) may be transmitted to the channel indicator 42 to illuminate and enhance visibility of the channel indicator 42. Additionally, in operation of the channel indicator system 64 (FIG. 14), the controller 67 may indicate the circumferential position of the instrument channel 20 which is selected for insertion of the instrument shaft 61 on the monitor 68 (FIGS. 14 and 15) via input from the sleeve position sensor 66 and the channel position sensor 65 that corresponds to the circumferential position of the selected instrument channel 20, as was heretofore described. Upon conclusion of the surgical operation, the instrument shaft 61 of the surgical instrument 58 may be withdrawn from the instrument channel 20 in the insertion portion 16 and from the selector channel 30 in the channel selector sleeve assembly 26, respectively. The insertion portion 16 of the endoscope 1 is removed from the body cavity of the patient and post-operative procedures may be carried out.

Referring next to FIGS. 17-22 of the drawings, an alternative illustrative embodiment of the endoscope is generally indicated by reference numeral 90. As illustrated in the cross-sectional views of FIGS. 18 and 19, a viewing conduit 6 and an irrigation conduit 7 may extend through the operation conduit 3 of the operation portion 2, as was heretofore described with respect to the endoscope 1 in FIGS. 1-16. At least one light conduit 9 may additionally extend through the operation conduit 3 of the operation portion 2. The light conduit or light conduits 9 may be disposed in optical communication with a light source 78 (FIG. 16) of the endoscope control system 70.

Figure 20:
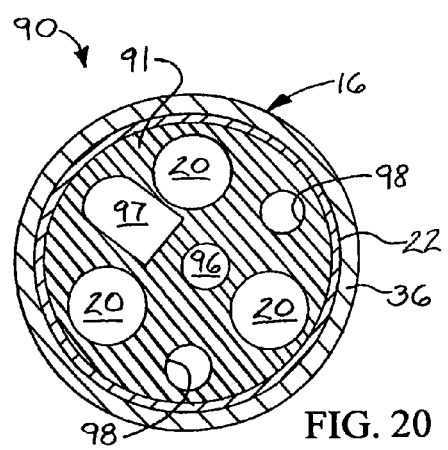
FIG. 20 is a sectional view of an insertion portion of the alternative illustrative embodiment of the endoscope, taken along section lines 20-20 in FIG. 17.

As illustrated in the cross-sectional view of FIG. 20, the insertion portion 16 of the endoscope 90 may include an elongated, flexible insertion portion body 91 which extends from the operation portion 2 of the endoscope 90. Multiple instrument channels 20 may extend longitudinally through the insertion portion body 91 in generally parallel, spaced-apart relationship to each other. In some embodiments, three instrument channels 20 may extend through the insertion portion body 91 in equally spaced-apart relationship with respect to each other (120 degrees) at generally the outer portion of the insertion portion body 91. as shown. Rotation of the channel selector sleeve assembly 26 facilitates registration of the selector channel 30 (FIG. 19) with a selected one of the instrument channels 20, as was heretofore described with respect to the endoscope 1 in FIGS. 1-16.

As illustrated in FIG. 20, a viewing conduit 96 may extend longitudinally through the insertion portion body 91 such as generally at the center or off-center with respect to the center of the insertion portion body 91, for example and without limitation. The viewing conduit 96 is disposed in optical communication with the viewing conduit 6 (FIG. 18) in the operation conduit 3 of the operation portion 2. An irrigation conduit 97, disposed in fluid communication with the irrigation conduit 7 (FIG. 18) in the operation conduit 3, may extend longitudinally through the insertion portion body 91 generally alongside or adjacent to the viewing conduit 96. At least one light conduit 98 may extend longitudinally through the insertion portion body 91 in optical communication with the light conduit 9 (FIG. 18) in the operation conduit 3. In some embodiments, a pair of light conduits 98 may extend through the insertion portion body 91 in spaced-apart relationship with respect to each other, as illustrated in FIG. 20. In some embodiments, the insertion portion body 91 may extend through a cylindrical or sleeve-shaped light conduit 22 which interfaces with the light transmission sleeve 34 (FIG. 19) of the channel selector sleeve assembly 26 to facilitate additional illumination of the insertion portion 16 during use of the endoscope 90, as was heretofore described with respect to the endoscope 1 in FIGS. 1-16.

Figure 21:
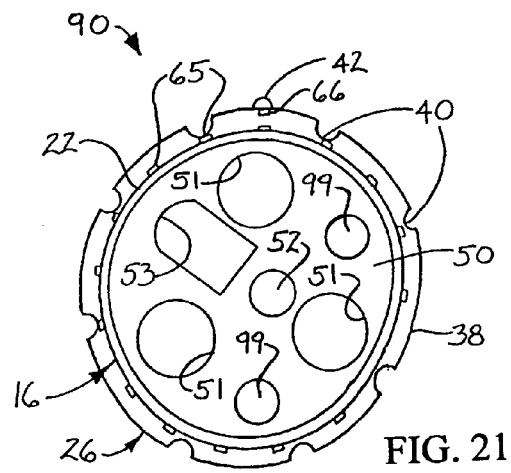
FIG. 21 is an end view of the insertion portion of the alternative illustrative embodiment of the endoscope, taken along viewing lines 21-21 in FIG. 17.

As illustrated in FIG. 21, channel openings 51 which communicate with the respective instrument channels 20 (FIG. 20) may be provided in an end cover 50 at the end of the insertion portion 16. A viewing window 52 may be provided in the end cover 50 at the viewing conduit 96. An irrigation nozzle 53 may be provided in the end cover 50 at the irrigation conduit 97 and directed generally toward the viewing window 52. A light lens 99 may be provided in the end cover 50 at each light conduit 98.

Operation of the endoscope 90 may be as was heretofore described with respect to the endoscope 1 in FIGS. 1-16, with the instrument channels 20 providing the selected positioning of the surgical instrument 58 (FIG. 9) about the circumference of the insertion portion 16 as the channel selector sleeve assembly 26 is first rotated on the operation portion 2 to align or register the selector channel 30 with the selected instrument channel 20 and the instrument shaft 61 of the surgical instrument 60 is inserted through the selector channel 30 and registering instrument channel 20, as illustrated in FIG. 13. The light lens 99 facilitate illumination of the surgical or examination field whereas the viewing window 52 facilitates viewing of the field. Irrigation fluid (not illustrated) may be periodically dispensed from the irrigation nozzle 53 (FIG. 21) to rinse and clear the viewing window 52.

Figure 22:
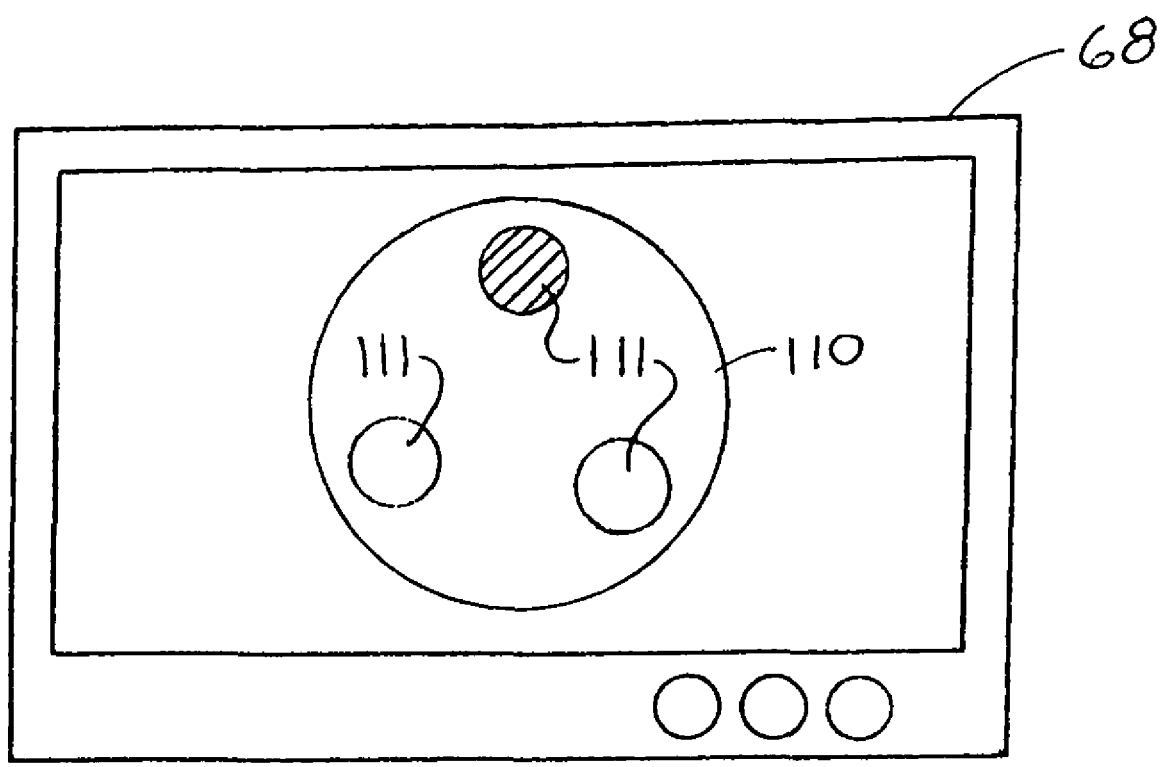
FIG. 22 is a front view of a monitor with multiple instrument channel images displayed on the monitor and one of the instrument channel images highlighted to indicate selection of a corresponding instrument channel.

As illustrated in FIG. 22, in some embodiments an insertion portion image 110 which represents a cross-section of the insertion portion 16 may be presented on the monitor 68. Multiple instrument channel images 111 which represent cross-sections of the respective instrument channels 20 may be presented on the insertion portion image 110. The instrument channel 20 which is selected for alignment with the selector channel 30 in the channel selector sleeve assembly 26 may be indicated by highlighting of the corresponding instrument channel image 111 which represents the selected instrument channel 20.

In some embodiments, a suction conduit 8 (FIG. 2) may additionally extend through the operation conduit 3 of the operation portion 2. At least one suction conduit (not illustrated) may extend through the insertion portion body 91 in fluid communication with the suction conduit 8 of the operation portion 2. At least one suction nozzle 54 (FIG. 5) may be provided in the end plate 50 in proximity to the viewing window 52 to facilitate suction of discharged irrigation fluid (not illustrated) from the viewing window 52. In some embodiments at least one of the viewing conduit 6, the irrigation conduit 7, the suction conduit 8 and the light conduit 9 may be omitted from the operation conduit 3 and may instead join the viewing conduit 96, the irrigation conduit 97, the suction conduit (not illustrated) and/or the light conduit or light conduits 98, respectively, of the insertion portion 16 through a separate port or ports (not illustrated).

While various illustrative embodiments have been described above, it will be recognized and understood that various modifications can be made and the appended claims are intended to cover all such modifications which may fall within the spirit and scope of the disclosure.

What is claimed is:

1. An endoscope, comprising:
   an operation portion;
   an elongated, flexible insertion portion extending from said operation portion;
   a viewing conduit extending through said operation portion and said insertion portion;
   a plurality of instrument channels provided in and spaced around a circumference of said insertion portion;
   a channel selector sleeve assembly having a selector channel rotatably carried by said operation portion; and
   wherein said selector channel of said channel selector sleeve assembly registers with said plurality of instrument channels, respectively, as said channel selector sleeve assembly is rotated with respect to said insertion portion.

2. The endoscope of claim 1 wherein said operation portion comprises an operation conduit and wherein said viewing conduit extends through said operation conduit.

3. The endoscope of claim 1 wherein said insertion portion comprises a channel conduit having a channel conduit wall and an insertion conduit extending through said channel conduit, and wherein said plurality of instrument channels extends through said channel conduit wall of said channel conduit and said viewing conduit extends through said insertion conduit.

4. The endoscope of claim 3 further comprising a light conduit and wherein said channel conduit extends through said light conduit.

5. The endoscope of claim 1 further comprising a channel indicator system having a plurality of channel position sensors carried by said insertion portion and corresponding in position to said plurality of instrument channels, respectively; a sleeve position sensor carried by said channel selector sleeve assembly and interfacing with said plurality of channel position sensors; a controller interfacing with said plurality of channel position sensors and said sleeve position sensor; and a monitor interfacing with said controller.

\* \* \* \* \*